United States Patent
Winkowski et al.

(10) Patent No.: US 6,616,740 B2
(45) Date of Patent: Sep. 9, 2003

(54) LIQUID COMPOSITIONS OF IPBC IN POLYETHYLENE GLYCOL, POLYPROPYLENE GLYCOL OR POLYPROPYLENE GLYCOL GLYCERYL ESTERS

(75) Inventors: Karen Winkowski, Sayreville, NJ (US); Xianbin Liu, Basking Ridge, NJ (US); Claudinei A. Fava, Long Valley, NJ (US); Daniel H. Brown, Carteret, NJ (US)

(73) Assignee: ISP Investments Inc., Wilmington, DE (US)

( * ) Notice: Subject to any disclaimer, the term of this patent is extended or adjusted under 35 U.S.C. 154(b) by 0 days.

(21) Appl. No.: 10/313,420

(22) Filed: Dec. 6, 2002

(65) Prior Publication Data

US 2003/0109598 A1 Jun. 12, 2003

Related U.S. Application Data

(60) Provisional application No. 60/341,110, filed on Dec. 12, 2001.

(51) Int. Cl.[7] ................... A01N 47/12; A01N 47/10
(52) U.S. Cl. ................... 106/18.32; 106/18.35; 514/478; 514/479; 523/122
(58) Field of Search .............. 106/18.32, 18.35; 514/478, 479; 523/122

(56) References Cited

U.S. PATENT DOCUMENTS

| | | | | | |
|---|---|---|---|---|---|
| 4,276,211 | A | * | 6/1981 | Singer et al. | 524/200 |
| 4,323,602 | A | * | 4/1982 | Parker | 427/298 |
| 6,361,788 | B1 | * | 3/2002 | Antoni-Zimmermann et al. | 424/406 |
| 6,506,794 | B1 | * | 1/2003 | Sianawati et al. | 514/476 |

FOREIGN PATENT DOCUMENTS

| | | | |
|---|---|---|---|
| JP | 06-40819 | * | 2/1994 |
| JP | 10-158110 | * | 6/1998 |
| JP | 11-21205 | * | 1/1999 |

* cited by examiner

*Primary Examiner*—Anthony J. Green
(74) *Attorney, Agent, or Firm*—Walter Katz; William J. Davis; Marilyn J. Maue

(57) ABSTRACT

Liquid compositions consisting essentially of by weight, 0.1–50% IPBC in 99.9–50% polyethylene glycol, polypropylene glycol or polypropylene glycol glyceryl ester, or mixtures thereof, which do not contribute to the VOC of paints and coatings and is stabilized effectively against discoloration even at elevated temperatures or direct sunlight.

1 Claim, No Drawings

LIQUID COMPOSITIONS OF IPBC IN POLYETHYLENE GLYCOL, POLYPROPYLENE GLYCOL OR POLYPROPYLENE GLYCOL GLYCERYL ESTERS

CROSS-REFERENCE TO RELATED PATENT APPLICATION

This application is based upon Provisional Application Serial No. 60/341,110 filed Dec. 12, 2001.

BACKGROUND OF THE INVENTION

1. Field of the Invention

This invention relates to liquid compositions which do not contribute to the VOC of paints and coatings, which are stable against decoloration and, particularly, are a mixture of 3-iodo-2-propynyl butyl carbamate (IPBC) and polyethylene glycol (PEG), or propylene glycol (PPG) or propylene glycol glyceryl esters (PGGE), or their combinations.

2. Description of the Prior Art

Various methods and compositions have been described to stabilize biocidal compositions containing IPBC, for example, using UV absorbers and/or organic epoxides in a liquid vehicle, as shown in U.S. Pat. Nos. 4,276,211; 4,552,885; 5,938,825; 6,059,991 and 6,140,370. Organic solvents such as N-methyl pyrrolidone (NMP), Texanol® ester alcohols, and dimethyl oxide (DMSO) are typical solvents for IPBC. Singer, W. et al, in U.S. Pat. No. 4,276,211, for example, described paint compositions containing iodoalkyne carbamates which were color stabilized by addition thereto of selected epoxy compounds. However, none of these references provide a stable IPBC composition which is also low in volatile organic compounds (VOC). In many jurisdictions, the local regulatory authority has established very low limits on the amount of VOC released upon use of the product. It is therefore desirable to minimize the VOC of additives in all materials sold for use in these jurisdictions.

Tanaka, Y. et al, in Japanese application No. Hei 11 (1999)-21205, described a vinyl chloride resin molding composition, where the antimicrobial and antifungal agent IPBC was first dissolved in a polyalkylene glycol plasticizer to facilitate the molding process and disperse the IPBC uniformly throughout the vinyl chloride resin before molding. The vinyl chloride resin molding composition did not discolor substantially when kneaded at a temperature above 200° C. However, no paint and coating compositions were disclosed or suggested in this reference.

The use of biocides to protect paint formulations and coatings, is of great commercial importance. One biocide widely used in paint compositions is 3-iodo-2-propynyl butyl carbamate, also referred to as IPBC. Unfortunately, many biocidal compositions containing IPBC are susceptible to decomposition under conditions of high temperature and exposure to sunlight. The decomposition of IPBC typically results in the formation of a yellow or brown by-product and also reduces the efficacy of the additive.

Color instability can become evident when the compositions containing IPBC are stored for extended periods of time in a warehouse in warm climates or when exposed to sunlight. The color of such compositions will turn dark brown. The compositions thus will be unsuitable for use in certain systems in need of antimicrobial protection particularly white aqueous paints. Furthermore, decomposition of the IPBC can render the biocidal composition less effective in controlling microbial growth.

In addition to the tendency of IPBC compositions to darken in color upon storage, the incorporation of IPBC into various formulations can also produce yellowing of dried films upon exposure of the film to direct sunlight. Obviously, this discoloration is undesirable and limits the use of such IPBC compositions.

SUMMARY OF THE INVENTION

What is described herein is a liquid composition consisting essentially of by weight, 0.1–50% IPBC in 99.9–50% polyethylene glycol, polypropylene glycol or polypropylene glycol glyceryl, or mixtures thereof, which does not contribute to the VOC of paints and coatings, and is stabilized effectively against decoloration even at elevated temperatures or under direct sunlight.

DETAILED DESCRIPTION OF THE INVENTION

The present invention is illustrated in more detail by the following examples. All references to parts and percentages are based on weight unless otherwise indicated.

In one embodiment of the invention, the liquid compositions of the present invention were made by mixing about 0.1 to 50 parts of Fungitrol® 400 (IPBC) with about 99.9 to 50 parts of PEG, or PPG or PGGE which was previously heated to 50° C.

EXAMPLE 1

Comparative Tests of Invention Composition Against NMP (Heating)

Solutions were obtained by dissolving 40 parts of IPBC in 60 parts of PEG with a molecular weight of 400 (PEG 400) or N-methyl pyrrolidone (NMP) as previously described. The solutions were then heated for 20 days at 65° C. and the color of the solutions was evaluated using a Gardner color scale. The results are shown in Table 1.

TABLE 1

| Color Stability after Heating (20 days at 65° C.) | | | |
|---|---|---|---|
| | Gardner Color | | |
| Composition | Before exposure | After exposure | Color Difference |
| 40% IPBC in NMP | 7 | 18 | 11 |
| 40% IPBC in PEG-400 | 5 | 11 | 6 |

This example shows that upon heating, the wet composition of IPBC in PEG-400 yellows less than when dissolved in an organic solvent, such as NMP.

EXAMPLE 2

As Above (Direct Sunlight)

Forty percent solutions of IPBC were prepared as described in Example 1. The solutions were then exposed to direct sunlight for 85 days. Color changes of the solutions were evaluated using a Gardner color scale. The results are shown in Table 2.

TABLE 2

Color Stability after Sunlight Exposure for 85 Days

| | Gardner Color | | |
|---|---|---|---|
| Composition | Before exposure | After exposure | Yellow difference |
| 40% IPBC in NMP | 7 | >18 | >11 |
| 40% IPBC in PEG-400 | 5 | 12 | 7 |

This example shows that upon light exposure, the wet formulation of IPBC in PEG-400 yellows less than when dissolved in an organic solvent, such as NMP.

EXAMPLE 3

Results of Examples 1 and 2

The IPBC solutions from Example 1 and Example 2 were analyzed by HPLC. The results are shown in Table 3.

TABLE 3

Stability of IPBC in PEG-400

| Composition | Before exposure Time 0 | After Heat age for 20 days at 65° C. | After sunlight exposure for 85 days |
|---|---|---|---|
| 40% IPBC in NMP | 39.87 | 33.55 | 34.03 |
| 40% IPBC in PEG-400 | 39.55 | 37.29 | 36.54 |

This example shows the improved stability of IPBC in the PEG-400 formulation after heat/sunlight exposure.

EXAMPLE 4

Stability of IPBC in PEG, PPG and PGGE

Solutions were obtained by dissolving 20 parts of IPBC in 80 parts PEG-400 or N-methyl pyrrolidone (NMP) or propylene glycol (PG), or fatty acid methyl ester (FAME) or polypropylene glycol glyceryl ethers (PGGE) or polypropylene glycol 425 (PPG-425) as previously described. The solutions were then heated for 30 days at 50° C. or exposed to direct sunlight for 30 days. All solutions were analyzed by HPLC. The results are shown in Table 4.

TABLE 4

| Composition | Before exposure Time 0 | After Heat age for 30 days at 50° C. | After sunlight exposure for 30 days |
|---|---|---|---|
| 20% IPBC in NMP | 17.0 | <15.0 | 15.6 |
| 20% IPBC in PG | 19.7 | 15.9 | 16.5 |
| 20% IPBC in FAME | 20.7 | 19.8 | 16.5 |
| 20% IPBC in PEG-400 | 19.8 | 20.2 | 18.3 |
| 20% IPBC in PGGE | 19.8 | 19.5 | 18.2 |
| 20% IPBC in PPG-425 | 20.0 | 20.2 | 18.7 |

This example shows the improved stability of IPBC in the PEG-400, PPG and PGGE formulation after heat/sunlight exposure, and the improved stability of IPBC in FAME after heat exposure.

EXAMPLE 5

Stabilization of IPBC in Aqueous Paint Formulations

Liquid formulations containing 40% IPBC in 60% PEG-400 were prepared as described in Example 1. Other commercially available formulations (e.g. Fungitrol® 440, 40% IPBC from ISP) was also evaluated for comparison purposes. Each IPBC formulation was then incorporated into an aqueous paint formulation described in U.S. Pat. No 4,276,211 (Singer et al., 1981) col. 4, lines 36–42 ("PAINTS"). This aqueous paint formulation was shown to yellow in the presence of IPBC. The paint samples containing the IPBC formulations were heat-aged for two weeks at 50° C. Dry-film samples were prepared by casting 3-mil wet films on drawdown paperboard and air dried for 24 hours. The Yellowing Index was measured in accordance with ASTM D-1925 method. The difference in yellowing between the control (paint without IPBC formulation) and the paint with the IPBC formulation, ΔB, was calculated as the response for each test. The results are shown in Table 5.

TABLE 5

Dry-Film Color Stability after Heat Aging

| Formulation | % by wt. | Al (% by wt) | Yellowing Index | ΔB |
|---|---|---|---|---|
| Paint formulation | — | — | 14.02 | — |
| 40% IPBC in PEG-400 | 0.8 | 0.32 | 16.36 | 2.34 |
| Fungitrol 440 (40% IPBC) | 0.8 | 0.32 | 17.06 | 3.04 |

This example showed that yellowing of the dry paint films after heat aging paints containing different IPBC formulations decreased when IPBC in PEG-400 solution was used in the formulation.

EXAMPLE 6

VOC Content of Liquid Formulations Containing IPBC

A 20% IPBC solution was dissolved in PEG, PPG or PGGE as previously described in the above examples. The VOC content of each was determined according to ASTM D-2369-98, and compared to VOC levels determined under same testing conditions for some other commercial IPBC formulations. The results are shown in Table 6 below.

TABLE 6

VOC Levels (% by wt)

| 20% IPBC in PEG-400 | 20% IPBC in PGGE | 20% IPBC in PPG-425 | 20% IPBC Commercial IPBC |
|---|---|---|---|
| 4.7 | 5.2 | 9.2 | 96.6 |

These results show that IPBC formulations in PEG-400, PGGE or PPG-425 contain significantly less volatile organic compounds than other commercial formulations.

EXAMPLE 7

VOC Content of Paint Containing IPBC Liquid Compositions 2.5 g of different 20% IPBC liquid compositions were added to 100 g of commercial paints advertised to be low in VOC. The VOC content of the paint containing the various IPBC liquid compositions was then determined as described in Example 6. Results are shown in Table 7.

TABLE 7

Contribution to Paint VOC Levels

| Type of Paint | VOC of Commercial Paint (% by wt.) | PEG-400 IPBC (% by wt.) | Commercial IPBC (% by wt.) |
|---|---|---|---|
| | | Contribution to VOC | |
| Flat (Aqueous) | 0 | 0 | +2.2 |
| Semi-gloss (Aqueous) | 3.5 | 0 | +1.3 |

While the invention has been described with particular reference to certain embodiments thereof, it will be understood that changes and modifications may be made which are within the skill of the art.

Accordingly, it is intended to be bound only by the following claims, in which:

1. An aqueous paint formulation including an effective amount of a liquid composition having low volatile organic content (VOC), consisting essentially of, by weight, 0.1–50% 3-iodo-2-propynyl butyl carbamate in 99.9–50% polyethylene glycol, polypropylene glycol or polypropylene glycol glyceryl, or mixtures thereof, which does not contribute to the VOC of the paint, and which stabilizes the paint effectively against decoloration even at elevated temperatures or under direct sunlight.

* * * * *